United States Patent
Oren et al.

(10) Patent No.: US 8,672,954 B2
(45) Date of Patent: Mar. 18, 2014

(54) PIERCING IMPLEMENT PARTICULARLY USEFUL AS A MEDICAL IMPLEMENT FOR PIERCING BODY TISSUE, AND METHOD OF USING SUCH IMPLEMENT FOR APPLYING A SUTURE TO THE BODY TISSUE

(75) Inventors: Ran Oren, Kibbutz Gaaton-Doar-Na Oshrat (IL); Laurent Lafosse, Annecy-Le-Vieux (FR); Shai Nahmias, Nahariya (IL); Dan Moor, Kibbutz Gaaton-Doar-Na Oshrat (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 766 days.

(21) Appl. No.: 12/602,101

(22) PCT Filed: May 29, 2008

(86) PCT No.: PCT/IL2008/000731
§ 371 (c)(1),
(2), (4) Date: May 31, 2010

(87) PCT Pub. No.: WO2008/146291
PCT Pub. Date: Dec. 4, 2008

(65) Prior Publication Data
US 2010/0249806 A1    Sep. 30, 2010

Related U.S. Application Data

(60) Provisional application No. 60/924,738, filed on May 30, 2007.

(51) Int. Cl.
*A61B 17/04* (2006.01)
*A61B 17/10* (2006.01)

(52) U.S. Cl.
USPC .......................................... 606/144; 606/139

(58) Field of Classification Search
USPC .................................................. 606/139–148
See application file for complete search history.

(56) References Cited

U.S. PATENT DOCUMENTS 5,562,686 A * 10/1996 Sauer et al. .................. 606/144
5,961,530 A    10/1999 Moore et al.
(Continued)

FOREIGN PATENT DOCUMENTS

DE    29805703    8/1998
EP    0686375    12/1995
(Continued)

OTHER PUBLICATIONS

Translation of Notice of Reason for Rejection Dated Jun. 29, 2012 From the Japanese Patent Office Re. Application No. 2009-522415.
(Continued)

*Primary Examiner* — Corrine M McDermott
*Assistant Examiner* — Christina Lauer

(57) ABSTRACT

An implement, particularly useful as a medical implement for applying a suture to a body tissue, includes a handle and shaft formed with a pair of channels extending from the proximal end of the handle through the distal end of the shaft and through a pair of jaws carried at the distal end of the shaft. The pair of channels converge towards each other to a cross-over point, and then diverging away from each other where existing at the distal end of the shaft. The channels are dimensioned to enable a piercing instrument to be passed first through one of the channels to pierce the body with a first bore, and then through the other of the channels to pierce the body with the second bore, such that the two bores have entry ends precisely spaced a predetermined distance from each other, and exit ends precisely spaced a larger predetermined distance from each other.

21 Claims, 3 Drawing Sheets

(56) References Cited

U.S. PATENT DOCUMENTS

| | | | |
|---|---|---|---|
| 5,993,466 A * | 11/1999 | Yoon | 606/147 |
| 6,015,411 A | 1/2000 | Ohkoshi et al. | |
| 6,045,555 A | 4/2000 | Smith et al. | |
| 2002/0065526 A1 * | 5/2002 | Oren et al. | 606/139 |
| 2002/0099385 A1 | 7/2002 | Ralph et al. | |
| 2004/0122435 A1 | 6/2004 | Green et al. | |
| 2006/0167475 A1 * | 7/2006 | Bischof et al. | 606/144 |
| 2007/0073342 A1 * | 3/2007 | Stone et al. | 606/232 |

FOREIGN PATENT DOCUMENTS

| | | |
|---|---|---|
| EP | 0880938 | 12/1998 |
| EP | 1488747 | 12/2004 |
| FR | 2560764 | 9/1985 |
| JP | 10-508780 | 9/1998 |
| JP | 11-047175 | 2/1999 |
| JP | 2002-102236 | 4/2002 |
| JP | 2002-511301 | 4/2002 |
| RU | 2087133 | 8/1997 |
| WO | WO 96/15727 | 5/1996 |
| WO | WO 99/52453 | 10/1999 |
| WO | WO 2007/002432 | 11/2007 |
| WO | WO 2008/015670 | 2/2008 |
| WO | WO 2008/146291 | 12/2008 |

OTHER PUBLICATIONS

Restriction Official Action Dated Jan. 17, 2012 From the US Patent and Trademark Office Re. U.S. Appl. No. 12/375,422.
Communication Relating to the Results of the Partial International Search Dated Dec. 12, 2007 From the International Searching Authority Re.: Application No. PCT/IL2007/000952.
International Preliminary Report on Patentability Dated Feb. 3, 2009 From the International Bureau of WIPO Re.: Application No. PCT/IL2007/000952.
International Search Report Dated Apr. 15, 2008 From the International Searching Authority Re.: Application No. PCT/IL2007/000952.
International Search Report Dated Mar. 26, 2009 From the International Searching Authority Re.: Application No. PCT/IL08/00731.
Written Opinion Dated Apr. 15, 2008 From the International Searching Authority Re.: Application No. PCT/IL2007/000952.
Written Opinion Dated Mar. 26, 2009 From the International Searching Authority Re.: Application No. PCT/IL08/00731.
International Preliminary Report on Patentability Dated Jan. 21, 2010 From the International Bureau of WIPO Re.: Application No. PCT/IL2008/000731.
Examiner's Report Dated Apr. 4, 2012 From the Australian Government, IP Australia Re. Application No. 2007280012.
Official Action Dated Feb. 21, 2012 From the US Patent and Trademark Office Re. U.S. Appl. No. 12/375,422.
Patent Examination Report Dated Oct. 16, 2012 From the Australian Government, IP Australia Re. Application No. 2007280012.
Translation of Notice of Reason for Rejection Dated Nov. 2, 2012 From the Japanese Patent Office Re. Application No. 2010-509949.
Official Action Dated Feb. 6, 2013 From the US Patent and Trademark Office Re. U.S. Appl. No. 12/375,422.
Applicant-Initiated Intervie Summary Dated Mar. 20, 2013 From the US Patent and Trademark Office Re. U.S. Appl. No. 12/375,422.
Notice of Non-Compliant Amendment Dated Oct. 15, 2012 From the US Patent and Trademark Office Re. U.S. Appl. No. 12/375,422.
Notice of Allowability Dated Nov. 25, 2013 From the US Patent and Trademark Office Re. U.S. Appl. No. 12/375,422.
Requisition by the Examiner Dated Sep. 19, 2013 From the Canadian Intellectual Property Office Re. Application No. 2,660,292.

* cited by examiner

PIERCING IMPLEMENT PARTICULARLY USEFUL AS A MEDICAL IMPLEMENT FOR PIERCING BODY TISSUE, AND METHOD OF USING SUCH IMPLEMENT FOR APPLYING A SUTURE TO THE BODY TISSUE

RELATED APPLICATIONS

This Application is a National Phase of PCT Patent Application No. PCT/IL2008/000731 having International filing date of May 29, 2008, which claims the benefit of U.S. Provisional Patent Application No. 60/924,738 filed on May 30, 2007. The contents of the above Applications are all incorporated herein by reference.

FIELD AND BACKGROUND OF THE INVENTION

The present invention relates to an instrument for use in piercing a tissue with two bores having entry ends precisely spaced from each other a predetermined distance, and exit ends precisely spaced from each other a predetermined larger distance than the entry ends. The invention is particularly useful in medical implements for piercing body tissue, such as bone or other tissue, with two bores, and for applying suture to the body tissue. The invention is therefore described below with respect to such an application.

There are many medical procedures requiring the piercing of a body tissue, such as a bone, with two precisely spaced bores in order to apply a suture to the body tissue. This is particularly true in minimally invasive surgical procedures, such as endoscopic or arthroscopic procedures wherein the production of such two—precisely bores is especially difficult because of the limited access provided the surgeon in such surgical procedures.

OBJECTS AND BRIEF SUMMARY OF THE PRESENT INVENTION

An object of the present invention is to provide an implement for use in piercing a body with two bores which implement is particularly useful in endoscopic or microscopic surgical procedures requiring the application of sutures to the pierced body tissue. Another object of the present invention is to provide a method of piercing body tissue with two precisely spaced bores, and also to applying a suture through the bores.

According to one aspect of the present invention, there is provided an implement for use in piercing a body with first and second bores having entry ends into the body precisely spaced from each other a predetermined distance, and exit ends from the body precisely spaced from each other a predetermined larger distance than that of the entry ends, comprising:

a handle having a proximal end for manual grasping by a user, and a distal end;

a shaft having a proximal end connected to the distal end of the handle, and a distal end defining a first jaw for engaging one side of the body to be pierced;

and a second jaw moveable towards the first jaw for engaging the opposite side of the body to be pierced, and for clamping the body between the two jaws;

characterized in that the handle and shaft are formed with a pair of channels extending from the proximal end of the handle through the distal end of the shaft; the pair of channels converging toward each other to a cross-over point, and then diverging away from each other where exiting at the distal end of the shaft; the pair of channels being dimensioned to enable a piercing instrument to be passed first through one of the channels to pierce the body with the first bore when the body is clamped between the jaws, and then through the other of the channels to pierce the body with the second bore spaced from the first bore the predetermined distance at the entry ends of the two bores, and the predetermined larger distance at the exit ends of the two bores.

As indicated above, the invention is particularly useful in medical implements for piercing body tissue, whereupon the pair of channels would be dimensioned to guide a medical piercing instrument through them, such as a drill, trocar, wire or needle, and then a suture through them.

According to another aspect of the present invention, there is provided a method of applying a suture to a body tissue by utilizing the above-described medical instrument to grasp the body tissue between the first and second jaws of the implement; passing a medical piercing implement through one of the channels and then through the other of the channels to pierce the tissue with the first and second bores; and then passing a suture through the first channel, through the first jaw, through the first bore in the tissue, around the exit end of the first bore, into the exit end of the second bore, and then through the second bore, the second jaw, and through the second channel.

As will be described more particularly below, such a medical implement and method are particularly useful in minimally-invasive surgical procedures, such as endoscopic or arthroscopic procedures.

Further features and advantages of the invention will be apparent from the description below.

BRIEF DESCRIPTION OF THE DRAWINGS

The invention is herein described, by way of example only, with reference to the accompanying drawings, wherein:

FIG. 6b is an end view of FIG. 6a; and

Figure 1:
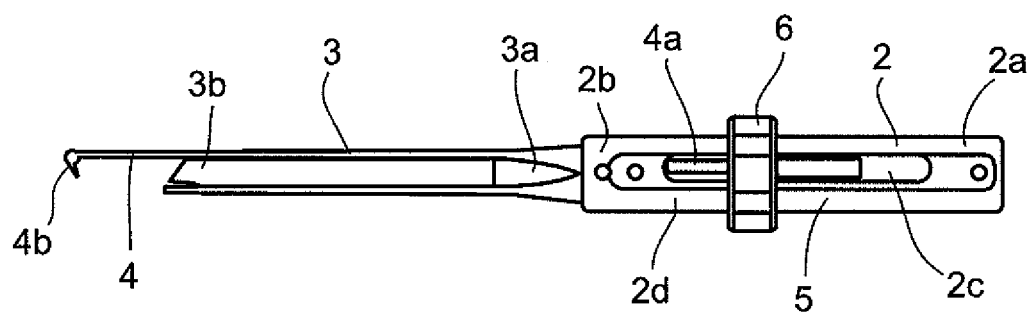
FIG. 1 is a side view illustrating one form of medical implement constructed in accordance with the present invention.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF THE PREFERRED EMBODIMENT

As indicated earlier, the invention is particularly useful as a medical implement for piercing a body tissue with two precisely-spaced bores for the application of a suture to the body tissue. In such use of the apparatus, the entry ends of the two bores must be precisely spaced from each other a predetermined distance, and the exit ends of the two bores from the body must be precisely spaced a predetermined larger distance than that of the entry ends, to provide a larger area of surface contact with the suture when passed through the entry end of one bore, around the exit ends of the two bores, and then back through the entry end of the other bore. The drawings thus illustrate a medical implement particularly useful in such a medical procedure, but it will be appreciated that the invention could also be used in non-medical applications requiring the formation of two bores precisely spaced from each other, e.g. for receiving a wire or the like.

The Construction of the Illustrated Medical Implement

As shown in FIGS. 1-5 of the drawings, the illustrated medical implement includes a handle 2 having a proximal end 2a for manual grasping by a user, and a distal end 2b; and a shaft 3 having a proximal end 3a connected to the distal end 2b of handle 2, and a distal end 3b. The distal end 3b defines a first jaw for engaging one side of the body to be pierced, shown in FIG. 5 as a bone B.

The illustrated medical implement further includes an elongated member 4, such as a rigid rod or strip, axially moveable with respect to shaft 3 and handle 2. Elongated member 4 has a proximal end 4a located within handle 2, and a distal end 4b formed with a hook formation to define a moveable jaw cooperable with the fixed jaw at the distal end 3b of shaft 3, to grasp the body member to be pierced, as will be described more particularly below.

The proximal end of elongated member 4 is coupled to a finger-piece 5 moveable within a slot 2c in handle 2, in order to move jaw 4b towards or away from the fixed jaw 3b. The distal end 2b of handle 2 is formed with external threads in order to threadedly receive a nut 6 which may be rotated in order to engage and retain finger-piece 5 in its position.

Figure 3:
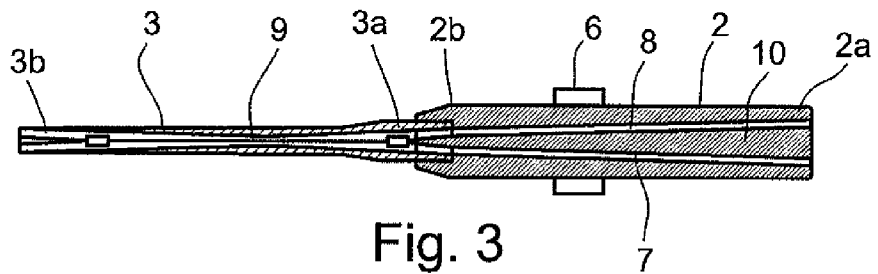
FIG. 3 is a longitudinal sectional view of the medical implement of FIGS. 1 and 2.
Figure 4:
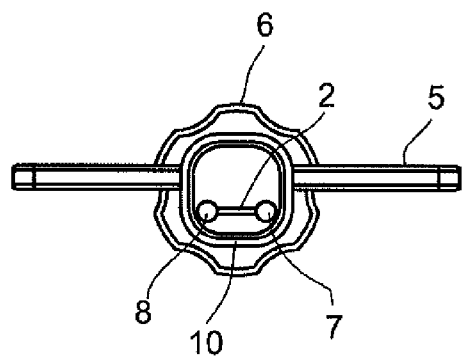
FIG. 4 is an end view, from the proximal end, of the medical implement of FIGS. 1-3.

As shown particularly in FIGS. 3 and 4, handle 2 and shaft 3 are formed with a pair of channels 7, 8 extending from the proximal end 2a of handle 2 through the distal end 3b of the shaft 3. The two channels 7, 8 are formed at a small angle to the longitudinal axis of the handle and shaft such as to converge towards each other at the distal end 2b of the handle, cross each other at a cross-over point 9 in an intermediate portion of shaft 3, and then diverge from each other at their exit ends at the distal end 3b of shaft 3.

Figure 5:
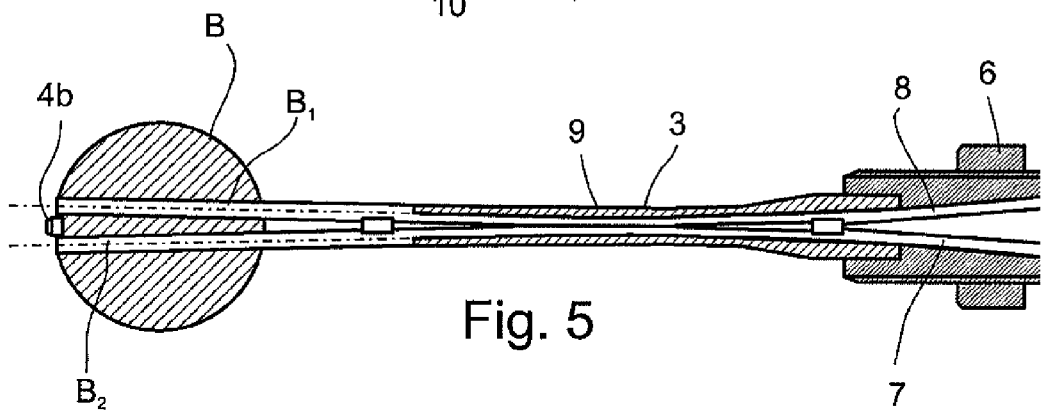
FIG. 5 is an enlarged fragmentary view illustrating the distal end of the medical implement of FIGS. 1-4, and particularly the manner in which the precisely spaced bores are formed in the body tissue, in this case bone tissue.
Figure 6B:
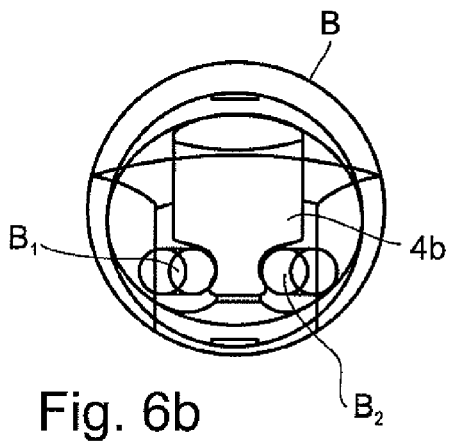
Figure 6A:
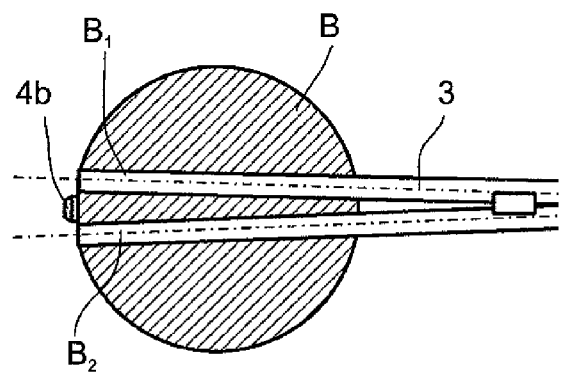
FIG. 6a is a further enlarged view of the distal tip of FIG. 5.

As will be described more particularly below, channels 7 and 8 are used for guiding a medical piercing instrument, such as a drill, trocar, wire or needle, to pierce the body tissue grasped between fixed jaw 3b at the distal end of shaft 3, and moveable jaw 4b of elongated member 4, with two precisely located bores. Thus, as shown in FIGS. 5 and 6a, the tissue involved is a bone B and is pierced by two bores $B_1$, $B_2$ which diverge away from each other from the entry end (right end, FIG. 5) of the bores, to the exit end (left end, FIG. 5) of the bores, such that the entry ends are spaced a predetermined distance from each other, and the exit ends are spaced a predetermined larger distance from each other. The latter spacing is particularly important to provide better support for a suture to be passed through the bores.

It will be appreciated that the spacings of the two bores may be precisely determined as desired for any particularly application by appropriately designing the angle and dimensions of the two channels 7, 8 through the handle 2 and shaft 3.

As will be further described below, the two channels 7, 8 are used, not only for producing the precisely-spaced bores through the body tissue, but also for applying a suture through the bores, first through one of the channels, and then back through the other of the channels. To facilitate application of the suture, the two channels are preferably interconnected by a slit shown at 10 in FIG. 4.

Method of Using the Described Implement

Figure 7:
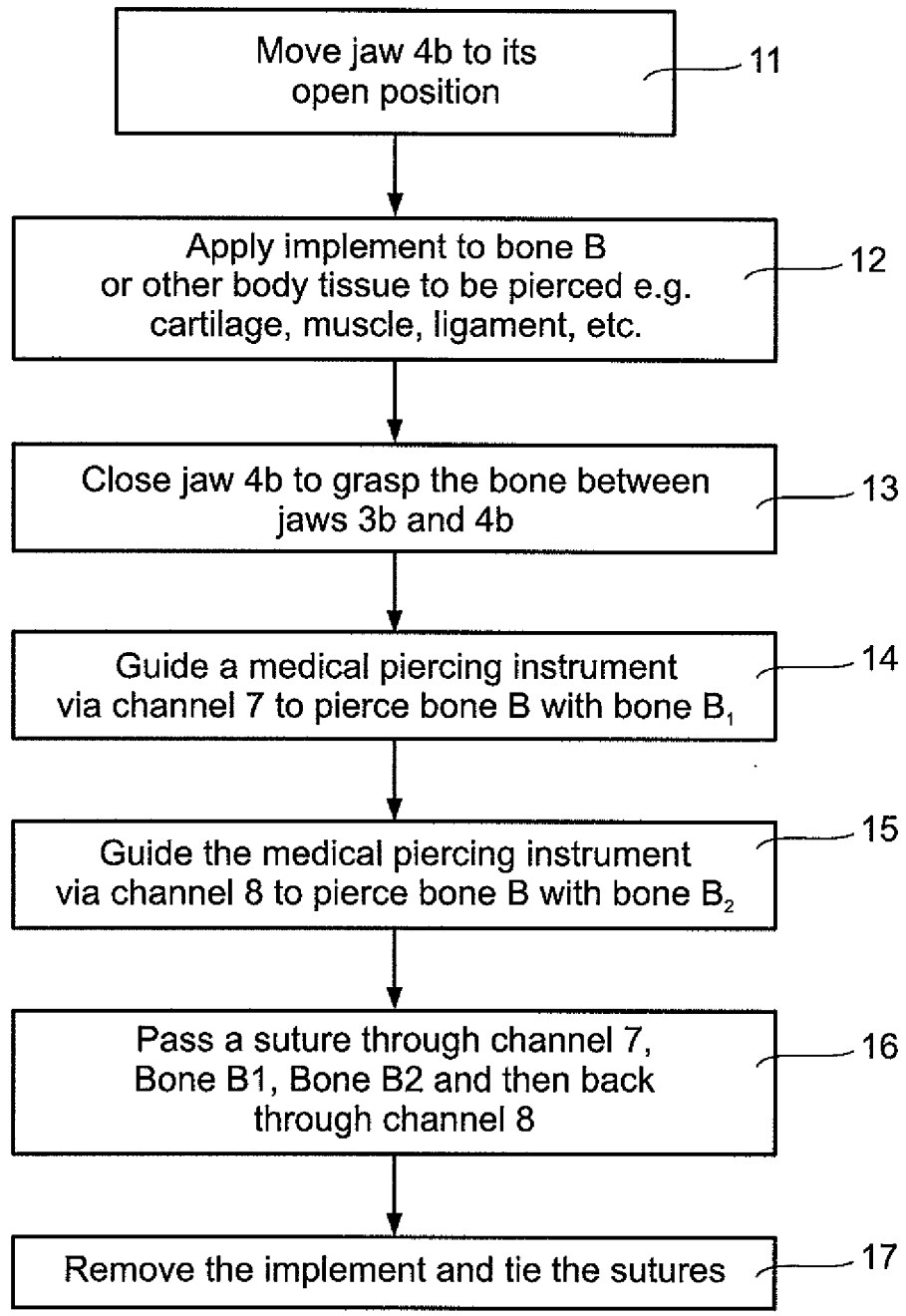
FIG. 7 is a flow chart illustrating the manner of using the implement of FIGS. 1-5 for applying a suture to a body tissue, such as a bone, cartilage, muscle or ligament tissue.

The method of using the implement of FIGS. 1-5 for producing the two precisely-spaced bores $B_1$, $B_2$ (FIG. 5) through the body tissue (B), and also for applying a suture through the so-produced bores, is now described particularly with respect to the flowchart of FIG. 7.

Figure 2:
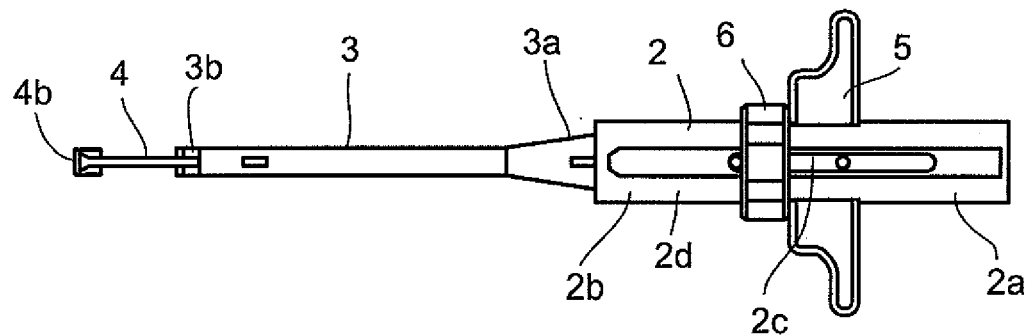
FIG. 2 is a top view of the medical implement of FIG. 1.

Thus, as shown in the flowchart of FIG. 7, moveable jaw 4b of the implement is moved to its open position, shown in FIGS. 2 and 3, by moving finger-piece 5 in the distal direction in slot 2c of the handle 2, preceded by threading nut 6 towards the distal end of handle 2 to retain the finger-piece in place (block 11, FIG. 7).

The implement is then applied to the body tissue, e.g. bone B FIG. 5, to be pierced (block 12); and jaw 4b is then closed by threading nut 6 towards the proximal end of handle 8 and moving hand-piece 5 against the nut, such that the bone B is grasped between the two jaws (block 13).

Channel 7 through handle 2 is then used for guiding a medical piercing instrument, e.g. a drill, trocar, wire or needle, to pierce the body tissue (e.g., bone B) with the first bore $B_1$ FIG. 5 (block 14); and then channel 8 is used in the same manner for guiding the piercing instrument to pierce the body tissue with the second bore $B_2$ (block 15).

The suture (not illustrated) is then passed, via channel 7, through bore $B_1$ through the exit (left) end of the bore $B_1$, and then through the exit end of bore $B_2$, and finally through channel 8 to the proximal end of handle 2 (block 16) such that the two ends of the suture are accessible to the surgeon for typing purposes.

Various known procedures may be used, such as by using suture leaders, suture manipulators, shuttles, or other suturing instruments for leading the suture through the body tissue via channel 7, and retrieving the suture from the body tissue via channel 8. As indicated earlier, slot 9 connecting the two channels together facilitates the foregoing movements of the suture.

While the invention has been described with respect to one preferred embodiment, it will be appreciated that this is set forth merely for purposes of example, and that many variations may be made. For example, shaft 3 may be formed with rectangular cuts or flues communicating with the bores for cleaning burns and sharp edges created when drilling the bores, or for removing debris when the implement is to be reusable. Disposable, single-use implement, e.g., made from plastics, would not require such flues.

Many other variations, modifications and applications of the invention will be apparent to those skilled in the art.

What is claimed is:

1. A medical implement for use in piercing a body portion with first and second bores having entry ends into the body portion precisely spaced from each other a predetermined distance, and exit ends from the body portion precisely spaced from each other a predetermined larger distance than that of the entry ends, comprising:

a handle having a proximal end for manual grasping by a user, and a distal end;

a shaft having a proximal end connected to said distal end of the handle, and a distal end defining a first jaw for engaging one side of the body portion to be pierced;

and a second jaw moveable towards said first jaw for engaging the opposite side of the body portion to be pierced, and for clamping the body portion between the two jaws;

wherein said handle and shaft are formed with a pair of channels extending from the proximal end of the handle through the distal end of the shaft; said pair of channels converging toward each other to a cross-over point, and then diverging away from each other where exiting at the distal end of the shaft; said pair of channels being dimensioned to enable a medical piercing instrument to be passed through either of said channels to pierce the body portion clamped between said jaws.

2. The medical implement according to claim 1, wherein said proximal end of the handle includes a finger-piece coupled to said second jaw for moving said second jaw towards and away from said first jaw.

3. The medical implement according to claim 2, wherein said finger-piece is slidably moveable along said handle and is coupled to said second jaw via an axial slit formed in said handle.

4. The medical implement according to claim 3, wherein said handle further includes a threaded section on the distal side of said finger-piece threadedly receiving a nut for retaining the finger-piece in its moved position.

5. The medical implement according to claim 1, wherein said second jaw is in the form of a hooked end of an elongated member moveable axially with respect to said shaft and handle.

6. The medical implement according to claim 1, wherein said channels through said handle are interconnected by a slot.

7. The method of applying a suture to a body tissue, comprising:

utilizing the medical implement according to claim 1 to grasp the body tissue between the first and second jaws of the implement;

passing a medical piercing implement through one of said channels and then through the other of said channels to pierce the tissue with said first and second bores;

and then passing a suture through said first channel, through said first jaw, through said first bore in the tissue, around the exit end of said first bore, into the exit end of said second bore, and then through said second bore, said second jaw, and through said second channel.

8. The method according to claim 7, wherein said body tissue is a bone.

9. The method according to claim 7, wherein said body tissue is cartilage, muscle, tendon or ligament tissue.

10. The method according to claim 7, wherein said method further comprises passing a tied suture longitudinally along a slot interconnecting between said channels.

11. The medical implement according to claim 1, wherein said second jaw is positioned between said exit ends of said bores.

12. The medical implement according to claim 1, wherein said cross over point is dimensioned to enable the advancement of a suture therethrough.

13. The medical implement according to claim 1, wherein said cross over point is positioned at an intermediate portion of said shaft.

14. The medical implement according to claim 1, wherein said pair of channels are dimensioned to enable a medical piercing instrument to be passed first through one of said channels to pierce the body portion with said first bore when the body portion is clamped between the jaws, and then through the other of said channels to pierce the body portion with said second bore spaced from said first bore said predetermined distance at the entry ends of the two bores, and said predetermined larger distance at the exit ends of the two bores.

15. The medical implement according to claim 1, wherein said pair of channels are dimensioned first to guide a drill, trocar, wire, or needle therethrough, and then a suture therethrough.

16. The medical implement according to claim 1, wherein said first and second jaws are dimensioned to grasp bone tissue between them for piercing same with said first and second bores in order to receive a suture therethrough.

17. The medical implement according to claim 1, wherein said first and second jaws are dimensioned to grasp cartilage, muscle, tendon or ligament tissue between the jaws for piercing same with said first and second bores in order to receive a suture therethrough.

18. A method of clamping a portion of body tissue and piercing said portion with two bores, in a single engagement of the tissue, comprising:

clamping a portion of body tissue using a tissue grasping element of a clamping implement; passing a medical piercing implement through said clamping implement to pierce said clamped portion of body tissue with a first bore; and passing a medical piercing implement through said clamping implement to pierce the same clamped portion of body tissue with a second bore.

19. The method of claim 18, wherein said clamping implement comprises a pair of channels dimensioned to enable a piercing instrument to be passed therethrough.

20. The method of claim 18, further comprising passing a suture through said clamping implement, through said first bore, through said second bore, and back through said clamping implement.

21. The method of claim 20, further comprising tying a knot in said suture and passing it through a longitudinal slot of said clamping implement.

* * * * *